United States Patent [19]

Fourcart et al.

[11] Patent Number: 5,648,208

[45] Date of Patent: Jul. 15, 1997

[54] USE OF A COLLAGEN AS SOLID BINDING SUBSTRATE FOR A LIGAND CAPABLE OF REACTING SPECIFICALLY WITH AN ELEMENT TO BE DETECTED IN A BIOLOGICAL MEDIUM, REACTANT AND IMPLEMENTATION

[75] Inventors: Jean Fourcart, Fimes; Chantal Buffevant, Vernaison; Alain Huc, Ste. Foy Les Lyon, all of France

[73] Assignee: Coletica, Lyon, France

[21] Appl. No.: 433,805

[22] Filed: May 3, 1995

Related U.S. Application Data

[63] Continuation of Ser. No. 182,099, filed as PCT/FR92/00749, Jul. 30, 1992, published as WO93/03373, Feb. 18, 1993, abandoned.

[30] Foreign Application Priority Data

Aug. 1, 1991 [FR] France ................................ 91 09819

[51] Int. Cl.$^6$ .................................................. C12Q 1/70
[52] U.S. Cl. ........................ 435/5; 435/7.1; 436/523; 436/524; 436/525; 436/526; 436/528; 436/529; 436/533; 436/534; 436/814
[58] Field of Search ........... 435/4, 5, 7.1; 436/523–526, 436/528, 529, 533, 534, 814

[56] References Cited

U.S. PATENT DOCUMENTS

| 4,169,804 | 10/1979 | Yapel, Jr. | |
| 4,452,773 | 6/1984 | Molday | 424/1.1 |
| 4,601,896 | 7/1986 | Nugent | 424/36 |
| 4,708,933 | 11/1987 | Huang et al. | 436/518 |
| 4,874,813 | 10/1989 | O'Shannessy | 530/395 |
| 5,034,330 | 7/1991 | Yamori et al. | 435/288 |
| 5,079,172 | 1/1992 | Hari et al. | 436/518 |

FOREIGN PATENT DOCUMENTS

| 0023607 | 2/1981 | European Pat. Off. . |
| 0397542 | 11/1990 | European Pat. Off. . |
| 0439222 | 7/1991 | European Pat. Off. . |
| 2642329 | 8/1990 | France . |
| 4037724 | 6/1991 | Germany . |
| WO8303 102 | 9/1983 | WIPO . |

OTHER PUBLICATIONS

Bennington, *Saunders Dictionary & Encyclopedia of Laboratory Medicine and Technology* (Philadelphia, PA, W. B. Saunders Company, 1984), pp. 307–388. RB37.B45.

Yolken et al. "Enzyme Immunoassay for the Detection of Rotavirus Antigen and Antibody" in: Rose et al., *Manual of Clinical Laboratory Immunology* (Washington DC, American Society for Microbiology, 1986), Third Edition, pp. 573–577.

Yolken, R.H. et al. Enzyme Immunoassay for the Detection of Rotavirus Antigen and Antibody. In: Manual of Clinical Laboratory Immunology, N.R. Rose et al., eds. Washington, DC: American Society for Microbiology, 1986, pp. 573–577.

Rawn, J. David. Biochemistry New York: Harper & Row, 1983, pp. 97–99.

Pharmacia. Affinity Chromatography: Principles & Methods. Pharmacia Laboratory Separation Division, Uppsala, Sweden, 1986–8, pp. 17–21.

Mattiassen, B. et al. Novel Approaches to Enzyme–Immunoassay. In: Enzyme Immunoassay, E.T. Maggio, ed. Boca Raton, FL: CRC Press, 1987, pp. 221–222.

Primary Examiner—Christine M. Nucker
Assistant Examiner—Jeffrey Stucker
Attorney, Agent, or Firm—Cushman Darby & Cushman IP Group of Pillsbury Madison & Sutro LLP

[57] ABSTRACT

The invention relates to the use of collagen as solid binding substrate for a sensor called ligand or refining agent, capable of reacting specifically with an element to be detected in a biological medium, to form a specific complex.

Preferably, the solid substrate comprises atelocollagen or a mixture of atelocollagen and of polyholoside.

The invention thus makes it possible to provide a biological reactant of high specificity and of which the constituents are of natural origin. It can be used easily and quickly.

37 Claims, No Drawings

USE OF A COLLAGEN AS SOLID BINDING SUBSTRATE FOR A LIGAND CAPABLE OF REACTING SPECIFICALLY WITH AN ELEMENT TO BE DETECTED IN A BIOLOGICAL MEDIUM, REACTANT AND IMPLEMENTATION

This is a continuation of application Ser. No. 08/182,099, filed as PCT/FR92/00749, Jul. 30, 1992 published as WO93/03373, Feb. 18, 1993, now abandoned.

The present invention essentially relates to the use of collagen as solid binding substrate for a sensor capable of reacting specifically with an element to be detected in a biological medium, reactant and implementation method.

It is already known from US document YAPEL/3M U.S. Pat. No. 4,169,804 to produce magnetically responsive composite microparticles comprising a magnetically responsive material and a porous solid water-insoluble matrix selected from proteinaceous materials, polysacchafides and mixtures thereof.

The magnetically responsive material is dispersed throughout the permeable solid water-insoluble matrix (see the abstract and the claims in columns 11 and 12).

Said document also provides the use of said solid porous microparticles as matrix for inclusion of a water-insoluble enzyme (column 1, line 66 to column 2, line 2) or of a specific receptor such as a protein or an antibody (see column 2, line 63 to column 3, line 26).

The Applicant has already described in document FR-B1-2 642 329 the use of solutions of atelocollagen and of glycosaminoglycans for the production of microcapsules as well as cosmetic or pharmaceutical or food compositions containing them.

The present inventors have now discovered that collagen, and preferably atelocollagen, and better still a mixture of atelocollagen and polyholosides, constitutes a remarkable solid binding substrate for a sensor capable of reacting specifically with an element to be detected in a biological medium in order to form a specific complex which can then be detected by any detection means.

It is a main object of the present invention to solve the new technical problem consisting in providing a solid substrate exhibiting on its external surface a large number of reacting functions or groups, in order to allow the covalent bond of a specific sensor, preferably a specific sensor of an element to be detected in a biological medium particularly for purposes of analysis and/or qualitative or quantitative assay.

Another main object of the present invention is to solve the new technical problem consisting in providing a solid substrate for binding on its surface a specific sensor exhibiting very good mechanical properties allowing ready dispersion into various mediums, notably due to strong stirring without any substantial deterioration of its initial abilities or properties.

The present invention aims further at solving the new technical problem consisting in providing a solid binding substrate for a specific element to be detected in a biological medium, which is capable of allowing rapid mixing with the biological medium as well as ready separation from said biological medium, with a view to gaining substantial time in medical analyses for medical diagnosis purposes. The invention has solved said technical problems for the first time, in a simultaneous, simple, easy, reliable and inexpensive manner, usable on an industrial and medical scale.

The invention makes it advantageously possible, in a biological application, to provide sensitive and reproducible assays of substance present in biological fluids. Advantageously also, the invention finds an application in the detection of a human rotavirus and in assaying of HCG in a biological fluid such as serum.

Thus, in a first aspect, the present invention relates to the use of collagen, preferably atelocollagen, and better still a mixture of atelocollagen and of a polyholoside, as solid binding substrate for a sensor, known as ligand or refining agent, capable of specifically reacting with an element to be detected in a biological medium to form a specific complex which can thereafter be detected by any detection means.

According to an advantageous characteristic of this use, the collagen is used in the form of particles, spheres or capsules, preferably of a diameter ranging between about 5 and 500 µm (micrometers). Capsules and in particular microcapsules are preferred.

According to an advantageous characteristic of the invention, the collagen comprises atelocollagen, preferably in combination with a polyholoside, such as a glycosaminoglycan, dextran or chitosan.

Said solid substrate, when prepared from native collagen, can be produced in particle form by coagulation of droplets.

In the case of atelocollagen, the same procedure can be used.

In the case of a mixture of atelocollagen with a polyholoside, the solid particles are preferably obtained by interface crosslinking as described in Applicant's previous patent FR-B1-2 643 329.

In this case, the relative proportion of polyholoside with respect to atelocollagen advantageously varies between 15 and 50% by weight.

According to another advantageous characteristic of the invention, the particles of collagen contain a magnetic oxide, preferably a magnetic iron oxide.

Advantageously, the magnetic oxide concentration is comprised between 0.1 and 10 % by weight with respect to the total weight of particles.

According to another particular characteristic of the invention, said sensor is covalently bonded by a chemical agent on the particles of collagen forming solid binding substrate.

The solid substrate according to the invention has the advantage of presenting superficial chemical functions such as the amino (—$NH_2$), carboxylic —($CO_2H$) or alcoholic (—OH) functions, which make it possible to effect the bonding of the sensor forming ligand or refining agent.

Preferably, in the case of amino functions (—$NH_2$), the chemical bonding agent used between the sensor and the solid substrate, will be a reactant of NHS type (N-hydroxysuccinimide), one of which can be reacted with the amino group of the solid substrate and the other with the sensor forming ligand or refining agent. This bonding is preferably effected in two stages, the first stage consisting in bonding the reactant on the surface of the solid particles of the substrate, then, having eliminated the excess of chemical bonding reactant, in effecting the bonding of the sensor forming ligand or refining agent with the solid particles of the substrate obtained after the aforesaid first stage.

The chemical bonding agents are said to be homobifunctional if the second reacting group is also of NHS type, and heterobifunctional if the latter is different. One example of a different second reacting group is a maleimide group able to bind a molecule by a thiol function (—SH).

In the case of carboxylic functions, the chemical bonding reactants preferably use water-soluble agents of carbodiimide type. Thereagain, they are used according to a method in two stages. Carbodiimides are heterobifunctional agents giving a bond of a carboxylic (—COOH) and an amino function (—NH₂).

In the case of alcoholic functions, the technique preferably used comprises oxidizing the alcohol function into an aldehyde (CHO) by a smooth oxidizing agent, such as sodium periodate (NaIO₄). The aldehyde can then be reacted with an amino function (—NH₂) by forming a Schiffs base. Hereagain, this bonding is effected according to a method in two stages, the first stage consisting in oxidizing the alcohol function into aldehyde, the second stage consisting in effecting the bonding proper of the agent forming ligand or refining agent with the solid particles of the substrate obtained at the end of the first stage.

It is worth noting that, by using as solid substrate, collagen, atelocollagen, or an atelocollagen-polyholoside mixture, what is obtained is the presence, in large quantity, of various superficial functions on the particles of the solid substrate, which makes it easy to effect a bonding of different molecular populations on the same surface, such as for example an antibody and an enzyme.

Two methods may be used to this effect, i.e.

the mixing of different molecular populations during the bonding phase, which will induce the binding on the surface of the particles of the solid support of a variable part of said populations as a function of the particular reactivity of each population and of their respective concentration.

The result will then be a binding in a predetermined quantity of each population, and this in a reproducible manner, if the reaction conditions are reproduced.

On the other hand, the successive activation of the different functions available on the surface of the solid particles, followed by sequenced bonding of the different molecular populations, thereby making it possible to obtain a solid substrate with multiple specificity.

It will be further noted that according to the invention, the solid substrate is produced from natural substances extracted from animal tissues. This is the case with collagen and atelocollagen, which are long chain proteins extracted from the dermic tissue, as well as with polyholoside, particularly a glycosaminoglycan.

Thus the use according to the invention, of collagen, preferably atelocollagen and better still of an atelocollagen-polyholoside mixture, by binding a sensor forming ligand or refining agent, produces a reactant for the qualitative detection and quantitative measurement of any element whatsoever from a medium of biological origin. By element is meant in the present description and claims, any species of antibodies or antigens, in soluble or particulate form, as well as all the molecular species liable to create specific complexes for which the affinity constant is sufficiently strong to shift the reaction towards the formation of the complex.

Said reactant can be used in the conventional way with methods for the qualitative detection and quantitative measurement of an element in a medium of biological origin, in medical analyses for medical diagnosis purposes. Processing is easy and leads to a considerable gain of time due to a rapid mixing up with the biological medium and to a ready separation of the solid particles from said biological medium.

Said reactant enables the implementation of conventional methods known as "immuno-assays" in heterogeneous phase.

The reactant according to the invention enables the detection of elements present in infinitesimal quantity in a complex medium of biological origin due to the ability for the sensor forming ligand or refining agent, which is fixed on the solid phase, to extract and separate the element to be detected.

The medium of biological origin is normally a liquid phase constituted by a liquid of biological origin such as blood, urine, cephalorhachidian liquid, etc.; or an extract of tissue requiring the use of extraction means of a physical nature such as heat, radiation, etc.; or of a chemical nature such as enzyme, detergent, acid, base, etc.

The sensor forming binding or refining agent, which is fixed on the solid phase or solid substrate according to the invention is specific to the element to be detected and such sensors are wellknown to the man skilled in the art. Such sensors can, in adequate physico-chemical conditions, give rise to the formation of stable complexes notably by immuno-type reactions, which complexes are bonded on the surface of the solid phase and can thus be isolated from the other molecular populations which are present, by any type of method ending into the separation of the solid phase containing the complex bonded thereto.

The presence of the complex can thereafter be revealed by measuring the consumption using for example a technique of competition, or by measuring the proportionally bonded quantity of a labeled tracer which will give a specific signal measurable by a chemical or physical method such as isotopic count, spectrophotometry, luminometry, amperometry, etc. All said techniques are wellknown to the man skilled in the art.

In a second aspect, the invention thus covers as new products, a biological reactant characterized in that it comprises, as a solid substrate or phase, particles of collagen, preferably of atelocollagen, and better still, of a mixture of atelocollagen and polyholoside.

Different variants of embodiment of said reactant result from the foregoing description given in relation to the first aspect of the invention, and will also result from the following description given with reference to various non-restrictive examples of the invention.

In a third aspect, the present invention also covers a method for the detection in a biological medium, of an element to be detected.

According to an advantageous embodiment, the invention relates to a detection method characterized in that the biological reactant used is a biological reactant whose sensor is a human anti-rotavirus antibody, and in that the method is a method for detecting the human rotavirus.

According to another particular embodiment, the invention relates to a detection method characterized in that the biological reactant used is a biological reactant whose sensor is an anti-HCG antibody, and in that the method is a method for assaying the HCG in the serum.

Variants of embodiment of said method are also obvious from the foregoing description, as well as from the following description given with reference to the examples given hereinafter solely by way of illustration.

The polyholosides used are, in particular, glycosaminoglycans which are structural glycosaminoglycans selected from the group consisting of chondroitine-4-sulfate, chondroitine-6-sulfate, dermatane-sulfate, heparane-sulfate and keratane-sulfate, as well as heparin and its derivatives, particularly the derivatives of low molecular weight whose molecular weight can vary between 2,000 and 10,000. Chitosan and dextrane can also be used as polyholosides.

The polyholoside is used in particular in the form of aqueous solution at 0.5 to 4% and preferably 0.5 to 2%, and preferably still about 1%, by weight, with respect to the polyholoside solution.

The collagen, or preferably the atelocollagen, is preferably used in aqueous solution with a collagen or atelocollagen concentration comprised between 0.5 and 2% by weight. This solution of collagen or atelocollagen can be obtained by dissolving collagen or atelocollagen fibers in a slightly acid aqueous solution. Said slightly acid aqueous solution can be preferably an aqueous acid solution of 0.1M acetic acid. The atelocollagen can be obtained by enzymatic digestion of collagen wellknown to the man skilled in the art.

To prepare the mixture of collagen, and preferably atelocollagen, polyholoside, the polyholoside solution is advantageously introduced into the collagen and preferably atelocollagen solution. Then, the solid particles, in particular the microcapsules, are prepared according to a preparation method by interfacial crosslinking such as described in document FR-B1-2 642 329.

According to said methods, after homogeneously mixing the solution of collagen, preferably atelocollagen, with the polyholoside solution, an oily phase containing a crosslinking agent in dispersed phase form is dispersed into the continuous phase formed by the solution of a mixture of collagen, preferably atelocollagen and polyholoside, under stirring for the time required to obtain a suitable degree of interfacial crosslinking, thus permitting the production of microcapsules whose wall is a mixed wall of crosslinked collagen, preferably atelocollagen, and crosslinked polyholoside.

The microcapsules are separated in an appropriate way by a natural recantation after one or more washings if necessary.

It is also possible to proceed by extrusion of a laminar flow through an extrusion nozzle, the laminar flow being subjected to vibrations so as to form individual droplets which thereafter drop into a crosslinking bath containing the crosslinking agent.

Acid chloride, acid anhydride, or a dibasic or polybasic carboxylic acid are advantageously used as crosslinking agent. A preferred crosslinking agent is selected from the group consisting of terephtaloyl chloride, a phtaloyl chloride, a sebacoyl chloride, a succinyl chloride, a chloride of a tricarboxylic acid such as citric acid or an acid anhydride such as succinic anhydride.

A hydrophobic liquid is used as solvent of the crosslinking agent, in which liquid collagen, preferably atelocollagen and/or polyholoside, are insoluble. Cyclohexane or chloroform, are still preferably used.

Due to the use of an interfacial crosslinking method, it is thus possible to prepare microcapsules which can encapsulate any kind of active ingredient. In particular, it is advantageous to encapsulate in the microcapsules a magnetic particle such as an iron oxide, this enabling easy separation of the solid substrate from the solutions to be analyzed and constituting an important technical advantage of the invention. Indeed, a separation time less than 5 secs. is obtained over a 1 cm distance in the presence of a simple permanent magnet. This is due to their relatively important mass linked to a density close to 1 which requires only a small charge of magnetic oxide about 1% by weight, to reach that result. Then, magnetic stirring becomes possible. The solid substrate according to the invention has a relatively high volume which makes it unresponsive to the aggregation forces, whether of hydrophobic or ionic nature. This further enables rapid separation during production by low speed centrifuging, such as for example around 800 g for 2 mins., and resuspension in non-aggregated form by simple stirring.

The particles of the solid substrate according to the invention can be obtained in intermediate size for example of about 50 μm, due to the production method used, particularly interfacial crosslinking, thus enabling sufficient reacting surfaces to be obtained during an immunoassay (for example 625 $mm^2$ for 50 μl of particles of solid substrate in suspension at 10% by weight). Said external surface is permanently in contact with the reaction liquid. Therefore, it is an extremely efficient surface.

The particles of the solid substrate according to the invention are hydrophilic by nature, because of its chemical constitution. It is known that the polyholosides are chain formations of sugars having in their structure numerous hydrophilic functions. Moreover, it is also possible to incorporate chitosan as polyholoside, thus enabling solid particles to be obtained, which particles have a low ionic charge.

Moreover, the chemical covalent bonding according to the invention also enables graftings to be obtained, which graftings are strongly bonded, stable, and fixed in a selected direction, for example and advantageously for bonding peptides, this affording a maximum efficiency of reaction.

Other objects, characteristics and advantages of the invention will be more clearly understood from the following explanatory description given with reference to several examples of embodiment which are given solely for illustration purposes and therefore which cannot possibly limit the invention in any way.

In the examples, all the percentages are given by weight, except otherwise stated.

EXAMPLE 1 ACCORDING TO THE INVENTION

Bonding of polyclonal antibody with solid magnetic particles by EDC (1-ethyl-3-(3-dimethylaminopropyl) carbodiimide): application to the detection of human rotavirus in the stools.

1. Preparation of the Solid Particles (in microcapsule form)

Principle

Solid particles of average size, about 50 μm, were prepared and crosslinked after emulsion in an aqueous solution of atelocollagen and chitosan in an oily phase. Said preparation was made according to the method described in Example 1 of FR-B1-2 642 329 (89-01221). The incorporation of magnetic iron oxide (FE304) makes it possible to obtain a solid phase separable by action of a magnetic field.

Mode Operandi

To a 1.6% solution of atelocollagen are added 10% of a 3% solution of KITAN in lactic acid. The atelocollagen is prepared according to the method described in French Patent No. 89 01221.

The KITAN® is supplied by the company ABER TECHNOLOGIES, Prat Menau 29880 Plouguerneau France. The KITAN is a chitosan of molecular mass 1,200,000 daltons, having a desacetylation rate of 2.4%.

To the atelocollagen-Kitan mixture is added a 5% concentration of sodium carbonate. The pH is then adjusted to 8.0 with HCl N/10. In this preparation, 1% iron oxide $Fe_3O_4$ is introduced. 100 g of the resulting mixture are emulsified in 3900 ml of DRAGOXAT® sold by the German company DRAGOCO and containing 5% of SPAN 85® sold by ICI COMPANY. The emulsion is obtained by quick stirring with an Ultra Turax R stirring system, turning at 15,000 rpm for 2 hours.

400 Ml of DRAGOXAT® containing the crosslinking agent, i.e. 2.5% terephtalic acid chloride are added to the emulsion kept under stirring for 30 mins. at 15,000 rpm.

The crosslinking agent is eliminated by centrifuging at 1,500 g for 10 mins. and by rejection of the resulting supernatant.

Three successive washings are carried out with 400 ml of DRAGOXAT®, the collagenic capsules being recovered by centrifuging in the same conditions as before. Six washings, using each time 600 ml of ethanol are carried out in order to remove the residual DRAGOXAT. Two washings with 60 ml of a soda solution at pH 9 and three washings with de-ionized water enable the removal of the aggregates of capsules. A deposit of solid particles is thus obtained after centrifuging at 1,500 g for 10 mins.

Said deposit is then dispersed in an equal volume of de-ionized water containing 0.01% of sodium mercurothiolate. Such dispersion of solid particles will be that used in the detections and assays described hereunder.

2. Preparation of a Specific Reactant for an Immunoassay

Anti-rotavirus antibodies of gamma G type are used, which antibodies are purified from a hyperimmunized rabbit serum by a suspension of bovine rotavirus. The presence of anti-antigen antibodies of the virus group enables the detection of the human virus. The purity of the gamma globulins is checked by electrophoresis. The protein assay in weight/volume is effected by Lowry's technique.

The bonding of the antibodies on the solid magnetic particles obtained in stage 1 hereinabove is performed by using the carboxylic functions (—COOH) of collagen.

The solid particles are washed beforehand in a buffer of pH close to neutrality (comprised between 7 and 7.5) of low ionic strength and free from amine (such as for example: 10 mM Hepes buffer).

The solid particles are activated by a soluble carbodiimide (for example EDC (1-ethyl-3-(3-dimethylaminopropyl) carbodiimide) at a concentration varying between 5 and 100 mM (for example 20 mM) diluted in the 10 mM Hepes buffer.

The proportion will be 1 volume of solid magnetic particles for 1 volume of EDC. The activation will take place under moderate stirring (for example on a rotary agitator) of the suspension for 1 hour between 20° and 25° C. The excess of EDC is thereafter eliminated by washing of the solid particles in a 10 mM Hepes buffer (4 successive washings by addition of 9 volumes of buffer) and recovery of the solid particles by centrifuging or by magnetism.

The bonding of the gamma G of the rabbit (dialyzed beforehand in a 0.15M Na solution) is performed by adding to the last centrifugation pellet 1 volume of 0.1M carbonate-bicarbonate buffer and 1 mg of gamma G per ml of pellet. The bonding is performed at room temperature on a rotary agitator for one hour.

Blocking of the residual functions is performed by adding 10% of the total volume of a 1M ethanolamine solution, of pH 9.0, and by stirring for one hour at between 20° and 25° C.

A sequence of 4 final washings with a 50 mM Tris buffer enables the elimination of the antibodies which have not been reacted and the 10% resuspension in said buffer makes it possible to obtain the final suspension of the specific reactant which is sought.

3. Detection of a Specific Element (forming reactant obtained in stage 2 above)

This preparation has been tested with regard to positive- and negative-labelled human stools for tracing the rotavirus. This prior classification was made with a reacting kit of the conventional ELISA type available on the market. The protocole of the immunological reaction with the aforesaid reactant of magnetic solid particles is as follows:

dilution of the stools to 3/30 in 50 mM Tris buffer—pH 7.4. Homogenization by stirring followed by centrifuging for 5 mins. to decant the fecal matter;

bringing together 400 µl of supernatant and 40 µl of 10% reactant of solid magnetic particles;

stirring for 20 mins on an oscillating agitator;

quick washings with 1 ml of Tween PBS buffer (Phosphate Buffer Saline) and separation of the solid phase by magnetization;

placing the recovered reactant of solid magnetic particles in contact with 500 µl of a monoclonal anti-rotavirus antibody; called "revealing" because conjugated with peroxydase;

stirring for 20 mins on an oscillating agitator;

quick washings with 1 ml of Tween PBS buffer, separation of the phases by magnetization;

revelation of the enzymatic activity by a chromogenous substrate: $H_2O_2$/orthophenylenediamine.

Reading is done visually, coloring intensity being assessed in +, see Table I below.

TABLE I

| Stools | Coloring | Interpretation |
|---|---|---|
| A | 0 | negative |
| B | ++++ | positive |
| C | ++++ | positive |
| D | 0 | negative |

EXAMPLES 2 ACCORDING TO THE INVENTION

Bonding of polyclonal antibodies to solid magnetic particles using EDC: application to assaying HCG (Human Chorionic Gonadotrophin) in serum.

The anti-HCG antibodies used are of gamma G type and are purified from serum from a rabbit hyperimmunized by total purified HCG. Said antiserum therefore comprises antibodies of specificity α and β. The bonding was performed according to the same protocole as in Example 1.1 and 1.2.

The reactant-forming preparation was tested with regard to human sera of pregnant women previously classified with the aid of a conventional ELISA kit found on the market. Two sera from masculine donors were used as negative control.

The protocole of the immunological reaction with the sensitized solid magnetized particles is as follows:

bringing together 50 µl of undiluted serum and 40 µl of reactant of solid magnetic particles at 10%;

stirring for 15 mins. on an oscillating agitator;

addition of 100 Al of an anti-HCG monoclonal antibody (specificity β) conjugated with peroxidase;

stirring for 15 mins. on an oscillating agitator;

quick washings with 1 ml of Tween PBS buffer, separation of the phases by magnetization;

revelation of the enzymatic activity by $H_2O_2$/orthophenylenediamine.

Reading is done on a spectrophotometer at 492 nm after blocking of the enzymatic reaction with 1 ml of sulfuric acid, see Table II below:

TABLE II

Assay of HCG in human sera

| | DO (492 nm) |
|---|---|
| II-A | |
| *Sera from pregnant women* | |
| 1 | 0.544 |
| 2 | 0.900 |
| 3 | 1.454 |
| 4 | 0.139 |
| 5 | 0.443 |
| II-B | |
| *Sera from masculine donors* | |
| a | 0.096 |
| b | 0.106 |
| Standard sera 5 mUI* (threshold of positivity) | 0.153 |

*mUI = International milli unit

Conclusion

The OD of the five positive sera is proportional to the concentration of the HCG present.

The sera from masculine donors are unquestionably negative (<threshold).

The solid magnetic particles are usable for a quantitative determination.

We claim:

1. A method of detecting the presence or absence of a substance in a biological medium comprising the steps of:
   providing a solid binding substrate in particulate form having at least an external surface comprising a crosslinked collagen component selected from the group consisting of crosslinked collagen, crosslinked atelocollagen, and a crosslinked mixture of atelocollagen and a polyholoside,
   covalently binding to said crosslinked collagen component a ligand specifically reacting with said substance in the biological medium,
   contacting said solid binding substrate with said ligand covalently bound to said crosslinked collagen component, with said biological medium to form a specific complex when said substance is present in said biological medium, and
   detecting the presence or absence of said specific complex.

2. A method of detecting the presence or absence of a substance in a biological medium comprising the steps of:
   providing a solid binding substrate in particulate form having at least an external surface comprising a crosslinked collagen component selected from the group consisting of crosslinked collagen, crosslinked atelocollagen, and a crosslinked mixture of atelocollagen and a polyholoside, said crosslinked collagen component being obtained by an interfacial crosslinking,
   covalently binding to said crosslinking collagen component a ligand specifically reacting with said substance in the biological medium,
   contacting said solid binding substrate with said ligand covalently bound to said crosslinked collagen component, with said biological medium to form a specific complex when said substance is present in said biological medium, and
   detecting the present or absence of said specific complex.

3. A method of detecting the presence or absence of a substance in a biological medium comprising the steps of:
   providing a solid binding substrate in particulate form of a size between 5 and 500 μm having at least an external surface comprising a crosslinked collagen component selected from the group consisting of crosslinked collagen, crosslinked atelocollagen, and a crosslinked mixture of atelocollagen and a polyholoside, said crosslinked collagen component being obtained by an interfacial crosslinking,
   covalently binding to said crosslinked collagen component a ligand specifically reacting with said substance in the biological medium,
   contacting said binding substrate with said ligand covalently bound to said crosslinked collagen component, with said biological medium to from a specific complex when said substance is present in said biological medium, and
   detecting the presence or absence of said specific complex.

4. The method of claim 3, wherein said ligand is selected from the group consisting of an antibody, an antigen and an enzyme.

5. A method of detecting the presence or absence of a substance in a biological medium, comprising the steps of:
   providing a solid binding substrate in particulate form having at least an external surface comprising a crosslinked mixture of atelocollagen and a polyholoside,
   covalently binding to said external surface of said crosslinked mixture of atelocollagen and polyholoside a ligand specifically reacting with said substance to be detected in the biological medium,
   contacting said solid binding substrate with said ligand covalently bound to said external surface, with said biological medium to form a specific complex when said substance is present in said biological medium, and
   detecting the presence or absence of said specific complex.

6. The method of claim 5, wherein the solid binding substrate in particulate form is selected from the group consisting of particles, spheres, capsules and microcapsules.

7. The method of claim 5, wherein the solid binding substrate in particulate form has a size between 5 and 500 μm.

8. The method of claim 5, wherein the relative proportion of polyholoside to atelocollagen is between 15 and 50% by weight.

9. The method of claim 4, wherein the solid binding substrate in particulate form contains a magnetic oxide.

10. The method of claim 9, wherein the magnetic oxide concentration is between 0.1 and 10% by weight.

11. The method of claim 5, wherein said binding is performed by a chemical agent reacting with functional groups of the crosslinked mixture selected from the group consisting of amino groups, carboxylic groups, alcoholic groups and mixtures thereof.

12. The method of claim 4, wherein the polyholoside is selected from the group consisting of a glycosaminoglycan, heparin, chitosan and dextran.

13. The method of claim 12, wherein the heparin is of low molecular weight, ranging between 2,000 and 10,000.

14. The method of claim 12, wherein the glycosaminoglycan is selected from the group consisting of chondroitin-4-sulfate, chondroitin-6-sulfate, dermatan sulfate, heparan sulfate and keratan sulfate.

15. The method of claim 5, wherein said ligand is selected from the group consisting of an antibody, an antigen and an enzyme, in soluble or particulate form.

16. The method of claim 15, wherein said antibody is selected from the group consisting of a human anti-rotavirus antibody and an anti-HCG antibody.

17. The method of claim 4, wherein said solid binding substrate has a multiple specificity for more than one of said ligands.

18. The method of claim 5, wherein said crosslinked mixture is obtained by interfacial cross-linking.

19. A biological reactant comprising a solid binding substrate in particulate form having at least an external surface comprising a crosslinked collagen component selected from the group consisting of collagen, atelocollagen and a mixture of atelocollagen with a polyholoside, on which external surface is covalently bonded a ligand specifically reactive to a substance to be detected in a biological medium.

20. A biological reactant comprising a solid binding substrate in particulate form having at least an external surface comprising a crosslinked mixture of atelocollagen with a polyholoside, on which external surface is covalently bonded a ligand specifically reactive to a substance to be detected in a biological medium.

21. A biological reactant comprising a solid binding substrate in particulate form having at least an external surface comprising a crosslinked collagen component selected from the group consisting of collagen, atelocollagen and a mixture of atelocollagen with a polyholoside, said crosslinked collagen component being obtained by an interfacial crosslinking.

22. A biological reactant comprising a solid binding substrate in particulate form of a size between 5 and 500 µm having at least an external surface comprising a crosslinked collagen component selected from the group consisting of collagen, atelocotlagen and a mixture of atelocollagen with a polyholoside, said crosslinked collagen component being obtained by an interfacial crosslinking.

23. The biological reactant of claim 19, wherein said solid binding substrate in particulate form is selected from the group consisting of particles, spheres, capsules and microcapsules.

24. The biological reactant of claim 23, wherein the solid binding substrate in particulate form has a size between 5 and 500 µm.

25. The biological reactant of claim 22, wherein the relative proportion of polyholoside to atelocollagen is between 15 and 50% by weight.

26. The biological reactant of claim 24, wherein the solid binding substrate contains a magnetic oxide.

27. The biological reactant of claim 23, wherein the magnetic oxide concentration is between 0.1 and 10% by weight.

28. The biological reactant of claim 19, wherein said binding is performed on functional groups of the mixture selected from the group consisting of amino functions, carboxylic functions, alcoholic functions and mixtures thereof.

29. The biological reactant of claim 22, wherein the polyholoside is selected from the group consisting of a glycosaminoglycan, heparin, chitosan and dextran.

30. The biological reactant of claim 29, wherein the heparin is of low molecular weight, between 2,000 and 10,000.

31. The biological reactant of claim 22, wherein said ligand is selected from the group consisting of an antibody, an antigen and an enzyme.

32. The biological reactant of claim 22, wherein said ligand is an antibody selected from the group consisting of a human anti-rotavirus antibody and an anti-HCG antibody.

33. The biological reactant of claim 22, wherein said solid binding substrate has multiple specificity for more then one of said ligands.

34. A method for detecting a human rotavirus in a biological medium comprising the steps of:

providing a solid binding substrate in particulate form having at least an external surface comprising a crosslinked component selected from the group consisting of crosslinked collagen, crosslinked atelocollagen and a crosslinked mixture of atelocollagen and a polyholoside, covalently binding on said external surface of crosslinked collagen component, a human anti-rotavirus antibody, contacting said solid binding substrate with said antibody, with said biological medium to form a human rotavirus-complex when said human rotavirus is present in said biological medium, and detecting the presence or absence of said human rotavirus complex, and thus the presence or absence of said human rotavirus in said biological medium.

35. The method of claim 34, wherein said solid binding substrate in particulate form contains a magnetic oxide, thereby enabling easy separation of the solid substrate from said biological medium for said detecting step.

36. A method for assaying HCG in a serum comprising the steps of:

providing a solid binding substrate in particulate form having at least an external surface comprising a crosslinked component selected from the group consisting of crosslinked collagen, crosslinked atelocollagen and crosslinked mixture of atelocollagen and a polyholoside, covalently binding on said external surface of a crosslinked collagen component, a human anti-HCG antibody, contacting said solid binding substrate with said antibody, with said biological medium to form a human HCG-complex when said human HCG is present in said biological medium, and detecting the presence or absence of said human rotavirus complex, and thus the presence or absence of said human rotavirus in said biological medium.

37. The method of claim 36, wherein said solid binding substrate in particulate form contains a magnetic oxide, thereby enabling easy separation of the solid substrate from the serum for said detecting step.

* * * * *